United States Patent [19]

Wu et al.

[11] Patent Number: 5,149,272

[45] Date of Patent: Sep. 22, 1992

[54] ASSAY FOR TOTAL AND DIRECT BILLIRUBIN

[75] Inventors: Yih-Shiong Wu, Carmel; Jeanne Bohannon; Yolanda White, both of Indianapolis; Mark J. Simmons, Carmel, all of Ind.

[73] Assignee: Boehringer Mannheim Corporation, Indianapolis, Ind.

[21] Appl. No.: 707,720

[22] Filed: May 30, 1991

[51] Int. Cl.$^5$ .................................... G01N 33/00
[52] U.S. Cl. ..................... 436/97; 436/903; 422/61
[58] Field of Search ............ 436/97, 903; 514/16; 422/61

[56] References Cited

U.S. PATENT DOCUMENTS

| | | | |
|---|---|---|---|
| 4,468,467 | 8/1984 | Babb et al. | 436/97 |
| 4,563,429 | 1/1986 | Doumas et al. | 436/97 |
| 4,665,038 | 5/1987 | Sakata et al. | 436/97 |

FOREIGN PATENT DOCUMENTS 8303254  9/1983  World Int. Prop. O.

OTHER PUBLICATIONS

Dappen et al., vol. 29/1, Clinical Chemistry, 37–41 (1983).
Sasaya et al., Patent Abstracts of Japan, vol. 5, No. 95, Jun. 1981.

*Primary Examiner*—Merrell C. Cashion, Jr.
*Assistant Examiner*—B. Celsa
*Attorney, Agent, or Firm*—Marilyn L. Amick; Max J. Kenemore; D. Michael Young

[57] ABSTRACT

Novel reagent compositions and an assay method for the measurement of total and direct bilirubin are disclosed. The reagent compositions comprise an aqueous solution of at least one betaine selected from the group of alkyl betaine, betaine and betaine hydrate, a sulfanilamide diazonium salt, iodide ions and sulfamic acid. In the measurement of total bilirubin, alkyl betaine serves as an accelerator/solubilizer for the reaction of unconjugated bilirubin, and the alkyl betaine, betaine or betaine hydrate, together with iodide ions, minimizes or substantially eliminates interference from hemoglobin and lipemia.

21 Claims, 10 Drawing Sheets

ASSAY FOR TOTAL AND DIRECT BILLIRUBIN

FIELD OF THE INVENTION

The present invention relates to the field of analytical chemistry, and particularly to that area concerned with the quantitative determination of bilirubin in a sample by the diazo method.

BACKGROUND OF THE INVENTION AND RELATED ART

Bilirubin is the principal pigment in blood serum and bile and is the product of the breakdown of hemoglobin and other heme-containing proteins. After formation in the reticuloendothelial cells of the spleen, bilirubin is transported to the liver in the form of a bilirubin-albumin complex. It is actively transported into the parenchymal liver cells, where most is reacted with n-glucuronate (and perhaps with other carbohydrates) to form water-soluble mono- and diglucuronides (conjugates). The water-soluble conjugates are actively transported from the parenchymal cells into the bile canaliculi of the gall bladder for excretion via the bile into the gastrointestinal tract.

The normal range for bilirubin in serum in nonjaundiced adults is 0.2–1.0 mg/dl, with 0.0–0.2 mg/dl normally present in the conjugated form. Elevations of serum bilirubin are reflected in clinical jaundice, which can be caused by hemolytic disorders such as acquired hemolytic anemia, reticulocytosis, parenchymal liver disease, obstruction of the bile excretory pathways, or by a deficiency of the enzyme UDP-glucuronyl transferase. Accordingly, sensitive and accurate assays for bilirubin are a useful and necessary tool in the diagnosis and treatment of a variety of hemolytic disorders, liver diseases and biliary tract disorders.

Undoubtedly the most widely used method for assaying or quantitatively determining bilirubin has been the diazo method, in which a sample suspected of containing bilirubin is contacted with a reagent composition which includes a diazonium salt. The diazonium salt reacts with bilirubin to form azobilirubin. The azobilirubin is reddish-violet in color at moderately acid or neutral pH conditions and has an absorption maximum of 540 nm, which is higher than that of bilirubin itself and is easily detectable by optical methods. Azobilirubin is blue in strongly acid or alkaline solution. The diazo method was introduced by Ehrlich in 1883 (*Charite Ann.* vol. 8, p. 140), who discovered that diazotized sulfanilic acid couples with bilirubin to give a yellow diazobilirubin pigment. In the absence of an accelerator, however, the reaction of unconjugated bilirubin is quite slow, and thus several modifications of Ehrlich's method have been devised to measure both conjugated (direct) and total bilirubin. In the Malloy-Evelyn modification (*J. Biol. Chem.*, vol. 119, p. 481, 1937), the conjugated bilirubin is measured 1 minute after the addition of Ehrlich's diazo reagent, whereas measurement of total bilirubin requires the addition of methanol as accelerator and a reaction time of 15 minutes. In the Jendrassik-Grof modification (*Biochem. Z.*, vol. 297, p. 81, 1938), caffeine and sodium benzoate serve as an accelerator/solubilizer instead of methanol. The blue azobilirubin formed is measured at 600 nm. Walters and Gerarde (*Microchem. J.*, vol. 15, p. 231, 1970) developed a method in which dimethylsulfoxide (DMSO) is used as the accelerator at low pH. Other workers have used ethylene glycol, propylene glycol, a non-ionic, sulfonated benzimidazole derivative with a high fatty acid radical, and dyphylline as accelerators and solubilizers for unconjugated bilirubin. For a variety of reasons, however, the presently used reaction solvents and accelerators all present certain disadvantages. Methanol causes precipitation of serum proteins, for example, and DMSO and ethylene glycol are quite viscous. Viscous substances impart flow characteristics to reagents containing them which make such reagents unsuitable for use with today's automated blood chemistry analyzers. In U.S. Pat. No. 4,404,286, Shull describes the use of tetramethylene sulfone (TMS) in his attempt to avoid the unacceptability of other solubilizers and accelerators.

Many other diazonium salts have been suggested. Certain 2,4- and 2,5-phenyldiazonium salts, for example, 2,4- and 2,5-dichlorophenyldiazonium salts have been used for the detection of bilirubin in serum and urine. In U.S. Pat. No. 3,754,862, Wahlefeld et al. (hereinafter Wahlefeld) describe a reagent comprising at least one of the group of chlorophenyl diazonium chlorides consisting of 2,4-dichloro-, 2,5-dichloro- or 2-chloro-4-nitrophenyl-diazonium chloride and, as a solubilizer, an alkyl-phenol polyethylene oxide. In Wahlefeld's method, the sample to be determined is added to a 2 to 10 volume percent solution of an alkylphenol polyethylene oxide in 0.01 to 0.2 M mineral acid, which contains 0.03 to 0.1 percent wt./vol. 2,4-dichloro-, 2,5-dichloro- or 2-chloro-4-nitrophenyl diazonium chloride, whereafter the absorbance is measured at 546 nm when the end color is reached. Wahlefeld was able to overcome several of the problems associated with methods using other diazonium salts and accelerators such as poor solubility or stability of the salt, unstable color formation, toxicity and high reagent viscosity. On the other hand, there remained several drawbacks. Wahlefeld's method has a linear range up to about 24 mg/dl bilirubin, and with levels greater than this limit, as are frequently seen with pediatric specimens, sample dilution is required. Another problem not avoided by Wahlefeld's method is interference in the assay from hemoglobin and indican that may be present in the sample. (Indican is a byproduct found in the sera of dialysis patients.) Furthermore, when adapting Wahlefeld's method to automated chemical analyzers that are in common use today, there may sometimes be an incompatibility of the reagent composition with metal needles and valves used for reagent aspiration and dispensing.

Another salt suggested for the determination of bilirubin is diazotized sulfanilamide. This diazonium salt also gives a reddish-purple azobilirubin in an acidic environment. As described by Chen et al. (*Clin Chem*, Vol. 26, No. 7, p. 990, 1980, hereinafter Chen), the working reagent for measuring total bilirubin contains 6 mM sulfanilamide, 1 mM sodium nitrite, 0.55 M oxalic acid, 25% N,N-dimethylformamide and 5% methanol. Babb et al. (hereinafter Babb), in U.S. Pat. No. 4,468,467, describe the use of certain substituted sulfanilamide and carbonamide diazonium salts for bilirubin assays using dry reagent compositions. Although Babb alludes to the utility of the described substituted sulfanilamide and carbonamide diazonium salts in reagent solutions for determining bilirubin, no actual working examples are described. In Chen's method, oxalic acid is used to maintain acidic reaction conditions and N,N-dimethylformamide is added to prevent serum protein precipitation. The linear range of Chen's method is up to 27 mg/dl of bilirubin; however, the stability of the reagent is only 48 hours at 4° C., and the method is also known to suffer from hemoglobin interference.

In U.S. Pat. No. 4,563,429, Doumas et al. (hereinafter Doumas) describe an improved conjugated (direct) bilirubin assay in which the sample to be assayed is pre-treated with a buffer containing iodide ions, thereby reducing the oxidation of hemoglobin to methemoglobin and preventing conjugated bilirubin from being oxidized to biliverdin. The iodide also prevents the destruction of the azopigment by the hemoglobin. Following this sample pre-treatment, the assay is conducted by adding diazo reagent, ascorbic acid, alkaline tartrate and a caffeine reagent.

SUMMARY OF THE INVENTION

In spite of these and numerous other variants, the test methods for determining direct and total bilirubin as previously described in the literature still do not satisfy all the necessary requirements. Accordingly, it is an object of the present invention to provide a reagent composition and assay method which avoids the problems which have plagued the prior art. More specifically, it is an object of the present invention to provide a reagent composition for determining bilirubin in which hemoglobin, lipemia and indican interference are substantially eliminated. It is a further object to provide a reagent composition which has flow characteristics suitable for use with today's automated blood chemistry analyzers and which is compatible with the materials used in the construction therein. Yet another object is to provide a reagent composition and assay which extends the range over which accurate bilirubin results may be obtained, and which reagent composition is stable and exhibits no blank reaction for at least four weeks. These and further objects and advantages of the present invention will become apparent to those familiar with the art of bilirubin assays upon reading the detailed description which follows and from the drawings.

The present invention provides a novel reagent composition for use in the measurement of bilirubin comprising at least one betaine selected from the group of alkyl betaine, betaine and betaine hydrate, a sulfanilamide diazonium salt, a source of iodide ions, and an acid, preferably sulfamic acid. In the measurement of total bilirubin, the reagent composition includes alkyl betaine, which serves as an accelerator for the reaction of unconjugated bilirubin, and, together with the iodide ions, minimizes or substantially eliminates interference from hemoglobin and lipemia. In the reagent composition, the sulfanilamide diazonium salt is generated by combining sulfanilamide with sodium nitrite or other source of nitrite ion in the acidic media. Total bilirubin in the sample, in the presence of alkyl betaine, is coupled with the sulfanilamide diazonium salt in the acid medium to form the azobilirubin pigment.

The alkyl betaine functions as a solubilizing agent for protein, unconjugated bilirubin and lipemia, as an inhibitor of hemoglobin peroxidase activity, and as a stabilizer for the iodide ions. The use of sulfamic acid helps to avoid problems of spurious results with certain synthetic calibration material that is currently in use. The prevention of indican interference that plagues the Wahlefeld method is accomplished by using the sulfanilamide diazonium salt, a non-chloro derivative. Optionally, effective amounts, generally less than 2 percent by weight, of nonionic surfactants such as octyl phenoxy polyethoxyethanol may also be added to the reagent composition for their known effects.

In the measurement of direct (conjugated) bilirubin, the reagent composition of the present invention comprises betaine or betaine hydrate, a sulfanilamide diazonium salt, a source of iodide ions, sulfamic acid and, preferably, trace amounts of a nonionic surfactant such as octyl phenoxy polyethoxyethanol. The use of betaine itself, or betaine hydrate, rather than alkyl betaine in the reagent composition allows the reaction of conjugated bilirubin but inhibits unconjugated bilirubin, which requires an accelerator. On the other hand, however, the betaine or betaine hydrate is still effective in the same manner as the alkyl betaine in stabilizing the iodide ion and eliminating hemoglobin interference. Betaines, including alkyl betaine, are internal salts which possess a quaternary ammonium ion which can form a complex with iodide ions, thereby protecting the iodide from decomposition.

When the reagent according to the present invention is present in a form ready for use as a solution for determining total bilirubin, the concentration of the alkyl betaine is preferably between 1 and 20 percent by weight. There is a wide concentration range over which beneficial effects are seen, and the exact amount of alkyl betaine can be adjusted by the individual depending upon the degree of effect desired. The preferred alkyl betaine contains a 12 to 14 carbon atom alkyl group. Longer or shorter alkyl group betaines should also be effective in reagent compositions according to the teachings of the present invention; however, none of such compounds are known to be commercially available at the present time.

The concentration of sulfamic acid used in the reagent according to the present invention is preferably between 0.01 and 0.5 molar. For measuring direct bilirubin, the acid concentration will be higher than that used for measuring total bilirubin. It is expected that acids other than sulfamic such as hydrochloric or other mineral acids may also be used in compositions of the present invention if certain limitations are of no concern, e.g., if interference of the reagent composition with metal instrument parts is not of concern to the practitioner of the present invention.

Almost any quantity of sulfanilamide diazonium salt will produce some kind of a reaction with bilirubin; however preferable concentrations of sulfanilamide diazonium salt in the reaction mixture will be less than 20 millimolar. Generally, increasing the concentration of sulfanilamide diazonium salt extends the range over which linear results will be obtained; however, at higher concentrations, precipitation of the salt may occur. Diazonium salts other than sulfanilamide may also be expected to be useful in the present invention if certain drawbacks, e.g., indican interference, are not of concern.

Apart from the sulfanilamide diazonium salt, betaine or alkyl betaine, iodide ions and acid, reagent compositions according to the present invention can optionally also contain one or more stabilizing agents such as are frequently added during manufacture in order to prevent or retard deterioration of the components or to reduce or inhibit microbial growth. Such agents are not essential for the reagent according to the present invention, but their presence in the usual amounts does not have a disturbing effect.

To perform an assay according to the method of the present invention, a sample, usually serum or plasma, is contacted with the reagent composition, and after the development of the colored azobilirubin product has occurred, usually in less than five minutes, the amount of color formed is measured using optical methods, e.g., spectrophotometrically, and compared to the amount of color formed using samples containing known amounts of bilirubin.

DETAILED DESCRIPTION OF PREFERRED EMBODIMENTS

A preferred embodiment of the present invention for measuring total bilirubin provides two working reagent compositions which are combined together with the sample to form a reaction mixture. A first preferred working reagent composition comprises alkyl betaine, sulfamic acid, a source of iodide ions, and, optionally, a nonionic surfactant. A second working reagent composition comprises sulfanilamide diazonium salt and sulfamic acid. By replacement of the alkyl betaine in the first reagent composition with betaine itself, or betaine hydrate or betaine salts, the composition can be used for the measurement of direct bilirubin.

In an especially preferred embodiment, the first working reagent composition is formed by combining two stock reagents, one of which contains the appropriate amount of alkyl betaine, betaine or betaine hydrate, a source of iodide ions and surfactant, and the second of which comprises the dry sulfamic acid in the amount required for the working composition. This embodiment is especially suited for commercially manufactured reagents to provide for maximum shelf life. The second working reagent composition is also formed by combining two stock reagents, one of which contains the appropriate amounts of sulfanilamide and sulfamic acid, and the second of which comprises a metallic nitrite, e.g., potassium or sodium nitrite, and an optional inert filler such as potassium sulfate. To make the working reagents, the appropriate dry stock reagent is added to the corresponding liquid stock reagent.

In a further preferred embodiment, an assay of the present invention is performed with the aid of one of the automated blood chemistry analyzers which have become very common in hospital and other clinical laboratories. Examples of these are the many Hitachi analyzers, which currently include models 717, 736, 737, 747, 704 and 705. The reagents of the present invention are applied to the analyzer according to standard procedures for operating the instrument. Calibration and control samples are also utilized in the assay according to customary practices for laboratory testing.

To prepare a reagent composition for measuring total bilirubin according to the teachings of the present invention, a first working reagent (accelerator reagent) is prepared comprising an aqueous solution containing most preferably about 4–20 percent by weight alkyl betaine (e.g., EMIGEN BB, registered trademark of Albright & Wilson Limited for C12–C14 alkyl betaine), about 80–160 mM sulfamic acid, about 10–15 mM iodide and optionally about 1.2–1.6% by weight TRITON X-100 (registered trademark of Rohm & Haas for octyl phenoxy polyethoxyethanol, a nonionic surfactant).

A second working reagent (color reagent) is prepared comprising an aqueous solution containing preferably about 5–15 mM sulfanilamide, about 450–550 mM sulfamic acid, and about 10–30 mM metallic nitrite. The preferred quantities of the reactants in these working reagents for total bilirubin assay have been calculated to give a final reaction concentration, when applied to the Hitachi 717 or 747 analyzer as described more fully in the examples below, of about 8.6% alkyl betaine, about 188.2 mM sulfamic acid, about 9.8 mM iodide, about 2.45 mM sulfanilamide, about 5.3 mM nitrite and about 1.1% TRITON X-100. Those skilled in the art will easily recognize that one can change the sample and/or reagent volumes and, by then also making appropriate adjustments to the concentration of the reactive ingredients, still be able to perform an assay according to the teachings of the present invention.

To prepare a reagent composition for measuring direct bilirubin according to the teachings of the present invention, a first working reagent (acid reagent) is prepared comprising an aqueous solution containing preferably about 2–8 percent by weight betaine monohydrate, about 80–300 mM sulfamic acid, about 9–15 mM iodide and approximately 0.1–0.3% by weight TRITON X-100. A second working reagent (color reagent) for direct bilirubin is prepared comprising an aqueous solution containing preferably about 6–9 mM sulfanilamide, about 300–500 mM sulfamic acid, and about 12–18 mM nitrite. The preferred quantities of the reactants in these working reagents have been calculated to give a final reaction concentration, when applied to the Hitachi 717 or 747 analyzer as described more fully in the examples below, of about 2.6% betaine monohydrate, about 258 mM sulfamic acid, about 8.7 mM iodide, about 2.42 mM sulfanilamide, about 4.8 mM nitrite and about 0.13% TRITON X-100. Again, those skilled in the art will recognize that one can change the sample and/or reagent volumes and, by then also making appropriate adjustments to the concentration of the reactive ingredients, still be able to perform an assay according to the teachings of the present invention.

Example I: Preparation of Total Bilirubin Reagent

A working color reagent for total bilirubin analysis was prepared by combining the following ingredients in the following proportions: 1.2 g sulfanilamide, 24.3 g sulfamic acid, 0.9 g sodium nitrite, and sufficient deionized water to bring the total volume to 500 milliters. This reagent remained stable for at least four weeks under refrigeration. When manufacturing reagents for commercial use, the sodium nitrite, which is a dry ingredient, may be weighed into a separate container for later addition to a stock solution containing the sulfanilamide and sulfamic acid. It is convenient to add an inert, dry filler such as potassium sulfate to the small quantity of sodium nitrite for convenience in the manufacturing process. This dry mixture containing the appropriate amounts of sodium nitrite and potassium sulfate is added to the stock sulfanilamide solution, which is in liquid form, to prepare a four-week supply of working color reagent.

Five hundred (500) milliliters of a working accelerator reagent for total bilirubin analysis was prepared by combining the following ingredients in the following proportions: 55.0 g EMPIGEN BB (alkyl betaine), 7.0 g TRITON X-100, 1.0 g potassium iodide, 5.3 g sulfamic acid and sufficient deionized water to bring the total volume to 500 milliliters. This reagent also was found to remain stable for at least four-weeks under refrigeration. When manufacturing reagents for commercial use, or to reduce reagent preparation if stability of the reagent for longer than four weeks is required, a stock accelerator reagent containing alkyl betaine, TRITON X-100, potassium iodide and deionized water can be prepared, to which the appropriate amount of sulfamic acid in dry form is added to prepare a fresh supply of working reagent.

Example II: Assay for Total Bilirubin

An assay for total bilirubin was performed using an Hitachi Model 717 automated blood chemistry analyzer. The reagents were applied and the instrument was configured so that the final reaction mixture contained 4 μl sample, 250 μl working accelerator reagent and 65 μl working color reagent. The sample and accelerator reagent were mixed and a sample blank absorbance reading made. Color reagent was added and, following a delay time of about 5 minutes, the reaction mixture was measured spectrophotometrically at 570 nm and 660 nm and compared to the measurement obtained from the reaction of a reference material sample containing a known level of bilirubin.

Example III: Linearity of Total Bilirubin Results

Figure 1:
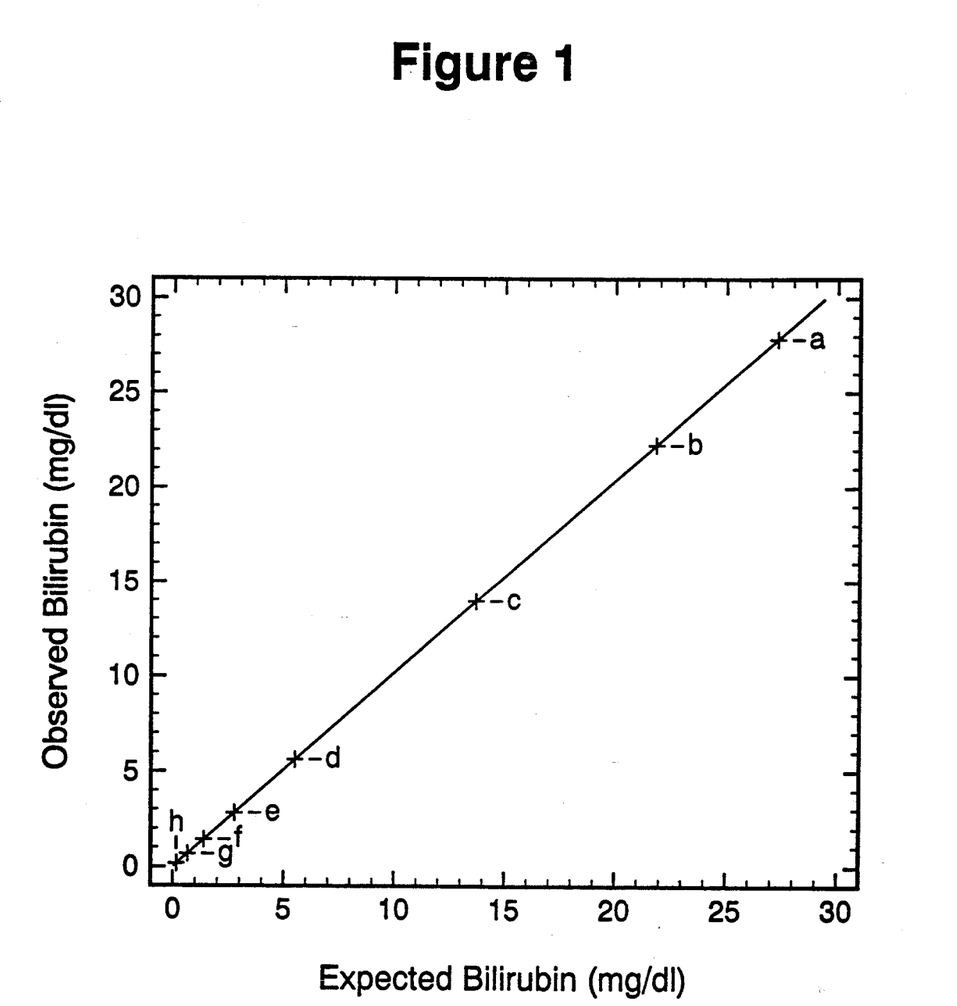
FIG. 1 is a graph illustrating linearity of total bilirubin results to greater than 30 mg/dl using the method of the present invention. Theoretical, or expected results are plotted on the x-axis and the observed results are plotted on the y-axis.

The method described above was used to assay a series of dilutions prepared from normal and very abnormal patient serum pools. Results obtained are shown in Table 1 below. FIG. 1 is a graph of these results which illustrates linearity of the results obtained using the present invention to at least greater than 30 mg/dl total bilirubin. The results obtained using the Wahlefeld method have been plotted along the x-axis and those obtained using the method of the present invention have been plotted along the y-axis and are illustrated in FIG. 1 as points a through i. Also shown in Table 1 are results obtained using the same patient pool samples and a Wahlefeld method assayed on the same instrument.

TABLE 1

Linearity - Total Bilirubin

| Sample | Dilution[1] | Present Invention (mg/dl) | Wahlefeld Method (mg/dl) |
|---|---|---|---|
| a | 100% | 28.27 | 28.34 |
| b | 80 | 22.68 | 22.80 |
| c | 50 | 14.39 | 14.40 |
| d | 20 | 6.11 | 6.05 |
| e | 10 | 3.12 | 3.15 |
| f | 5 | 1.71 | 1.78 |
| g | 2.5 | 1.06 | 1.15 |
| h | 1 | 0.66 | 0.76 |
| i | 0 | 0.38 | 0.49 |

[1]0% and 100% are normal and very abnormal patient serum pools respectively.

Example IV: Method Comparison of Total Bilirubin Assay

Figure 2:
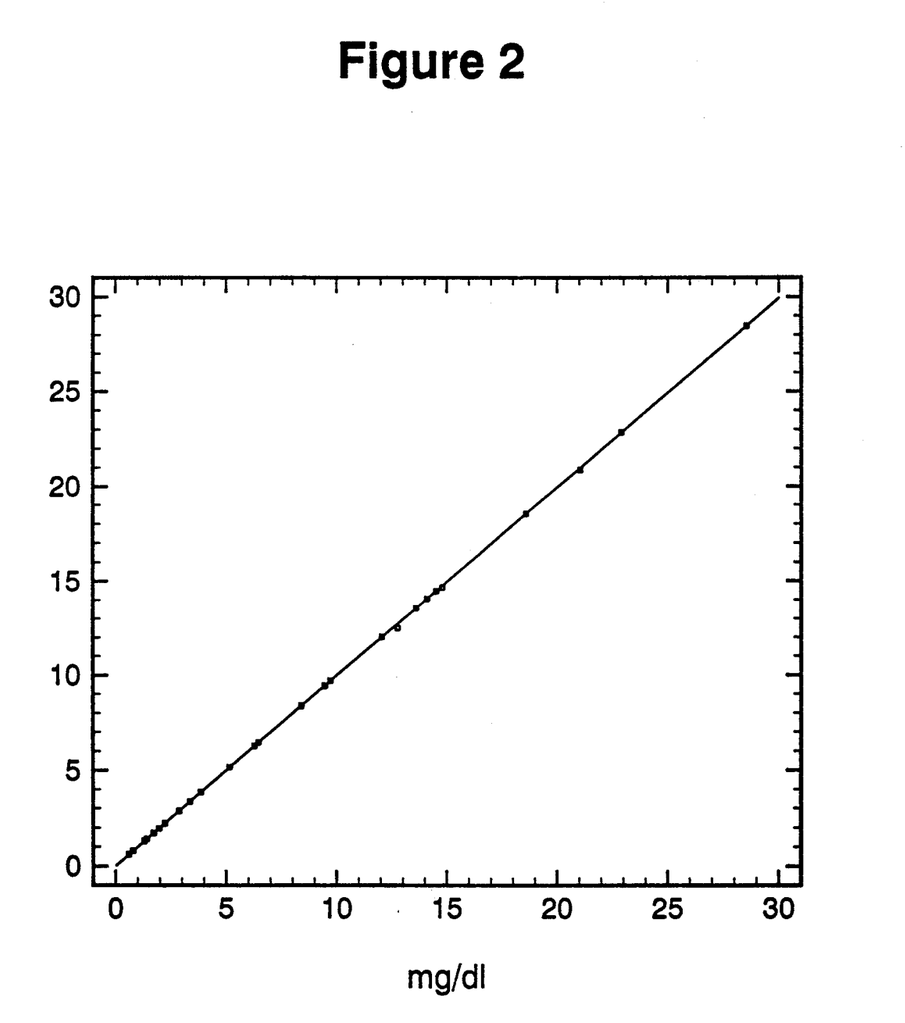
FIG. 2 is a graph showing correlation of total bilirubin results obtained using the method of the present invention with results obtained using a method which incorporates 2,5-dichlorophenyldiazonium tetrafluoroborate for the diazo reagent (hereinafter Wahlefeld method).

A method correlation study was performed by assaying a group of 29 patient serum samples using the method of the present invention and comparing the results obtained to the results obtained on the same samples assayed by a Wahlefeld method. Actual results obtained are given in Table 2 below. FIG. 2 is a graph of these results. Along the x-axis are plotted the results obtained using the Wahlefeld method, and the results obtained using the method of the present invention are plotted along the y-axis. Linear regression analysis showed a correlation coefficient of 0.999, with a slope of 0.999 and an intercept of −0.074.

TABLE 2

Method Comparison - Total Bilirubin

| Sample | Present Invention (mg/dl) | Wahlefeld Method (mg/dl) |
|---|---|---|
| 1 | 20.68 | 20.92 |
| 2 | 14.54 | 14.69 |
| 3 | 1.94 | 2.11 |
| 4 | 13.48 | 13.54 |
| 5 | 28.41 | 28.42 |
| 6 | 22.68 | 22.80 |
| 7 | 14.39 | 14.40 |
| 8 | 6.11 | 6.05 |
| 9 | 3.12 | 3.15 |
| 10 | 1.71 | 1.78 |
| 11 | 1.06 | 1.15 |
| 12 | 0.66 | 0.76 |
| 13 | 0.38 | 0.49 |
| 14 | 0.39 | 0.48 |
| 15 | 1.21 | 1.29 |
| 16 | 3.61 | 3.66 |
| 17 | 6.27 | 6.26 |
| 18 | 9.24 | 9.43 |
| 19 | 12.47 | 12.61 |

TABLE 2-continued

Method Comparison - Total Bilirubin

| Sample | Present Invention (mg/dl) | Wahlefeld Method (mg/dl) |
|---|---|---|
| 20 | 8.17 | 8.23 |
| 21 | 11.89 | 12.0 |
| 22 | 0.42 | 0.52 |
| 23 | 1.49 | 1.55 |
| 24 | 2.66 | 2.71 |
| 25 | 4.93 | 4.94 |
| 26 | 9.49 | 9.57 |
| 27 | 13.97 | 14.01 |
| 28 | 18.44 | 18.55 |
| 29 | 22.77 | 22.76 |

Example V: Hemoglobin Interference - Total Bilirubin

Hemoglobin interference studies were conducted using both the method of the present invention and the Wahlefeld method. Studies were conducted on a serum pool from normal patients, a pool having a total bilirubin value at the medical decision level, and a serum pool with an abnormally high level of bilirubin. Samples from these pools were spiked with varying amounts of hemoglobin up to 500 mg/dl and assayed by both methods. The results obtained are listed in Tables 3, 4 and 5 below.

Figure 3:
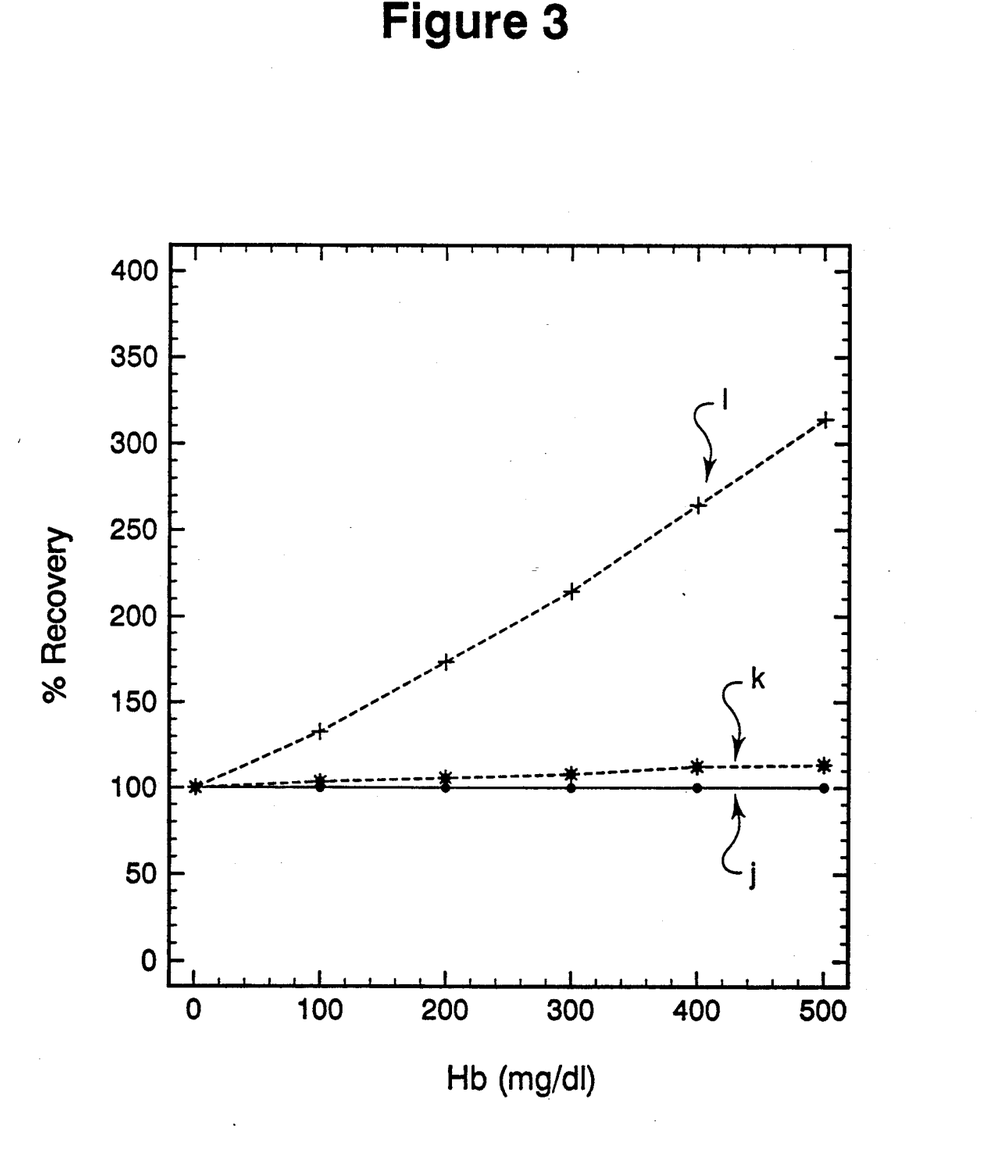
FIG. 3 is a graph showing hemoglobin interference with total bilirubin results obtained on a normal patient sample using the method of the present invention in comparison with those obtained using the Wahlefeld method.

FIG. 3 is a graph of the results obtained using the normal serum pool. The percent recovery is plotted on the y-axis and the amount of hemoglobin in mg/dl is plotted on the x-axis. Three curves have been plotted to represent the expected (theoretical) total bilirubin recovery, shown by line j; the recovery of total bilirubin obtained using the method of the present invention, shown by line k; and the recovery of total bilirubin using the Wahlefeld method, which is shown by line 1.

Figure 4:
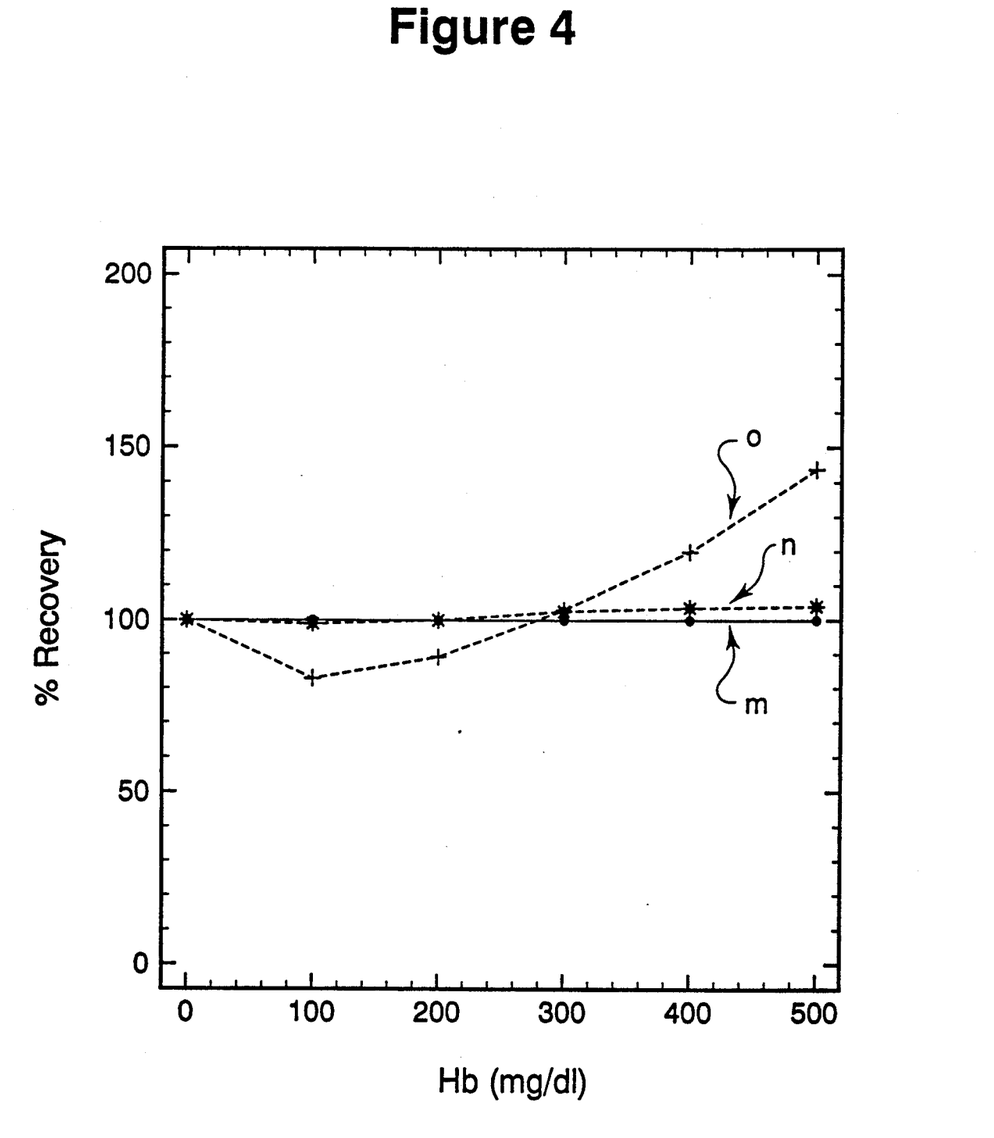
FIG. 4 is a graph showing hemoglobin interference with total bilirubin results obtained on a medical decision level sample using the method of the present invention in comparison with those obtained using the Wahlefeld method.

FIG. 4 is a graph of the results obtained using the medical decision level pool. The percent recovery is given on the y-axis and the amount of hemoglobin in mg/dl is given on the x-axis. Three curves have been plotted to represent the expected (theoretical) total bilirubin recovery, shown by line m; the recovery of total bilirubin obtained using the method of the present invention, shown by line n; and the recovery of total bilirubin using the Wahlefeld method, which is shown by line o.

Figure 5:
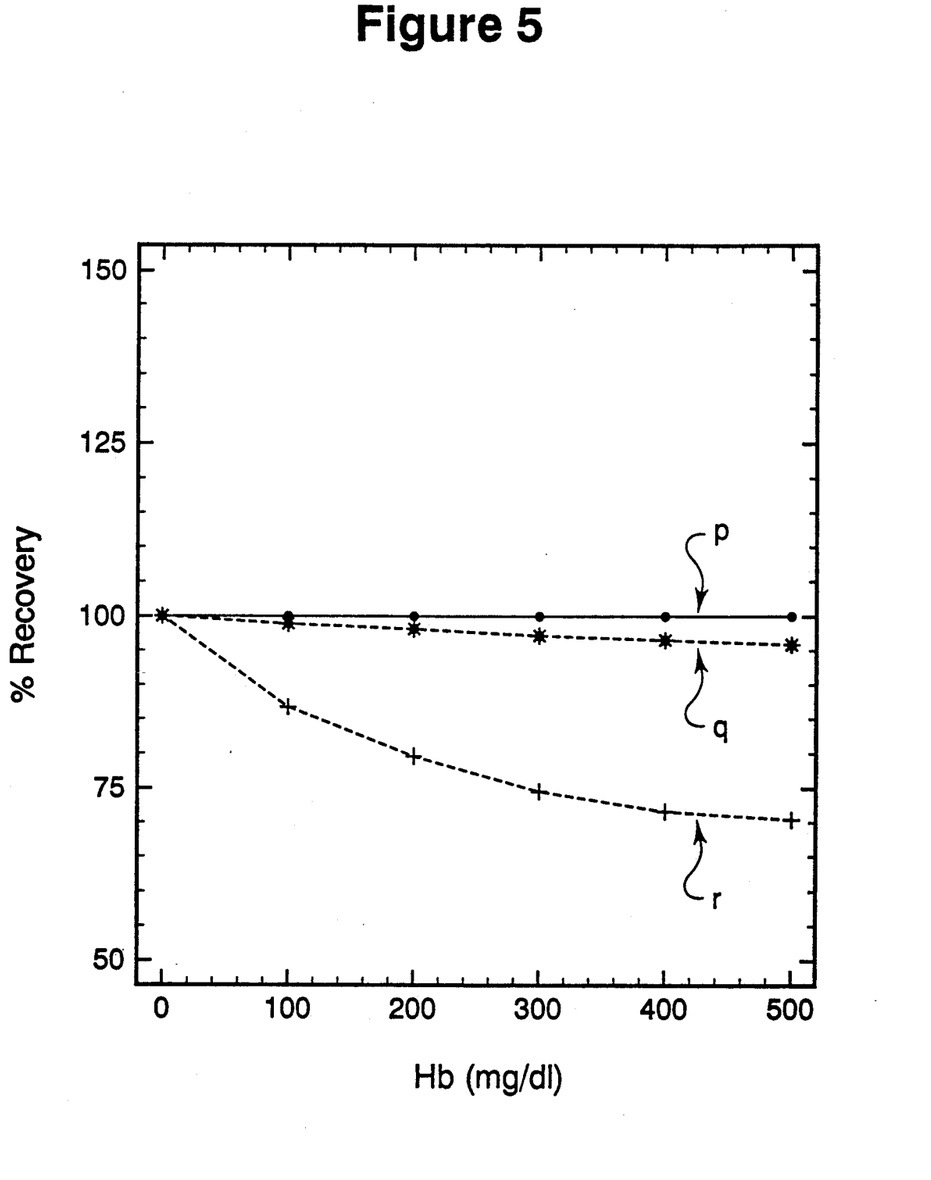
FIG. 5 is a graph showing hemoglobin interference with total bilirubin results obtained on a high patient sample using the method of the present invention in comparison with those obtained using the Wahlefeld method.

FIG. 5 is a graph of the results obtained using the high serum pool. The percent recovery is plotted on the y-axis and the amount of hemoglobin in mg/dl is plotted on the x-axis. Three curves have been plotted to represent the expected (theoretical) total bilirubin recovery, shown by line p; the recovery of total bilirubin obtained using the method of the present invention, shown by line q; and the recovery of total bilirubin using the Wahlefeld method, which is shown by line r.

TABLE 3

Hemoglobin Interference - Normal Serum

| Sample | Hb Level | Present Invention mg/dl | % Rec | Wahlefeld method mg/dl | % Rec |
|---|---|---|---|---|---|
| 1 | 0.0 | 0.51 | 100 | 0.635 | 100 |
| 2 | 100 | 0.52 | 102.0 | 0.837 | 131.8 |
| 3 | 200 | 0.53 | 106.4 | 1.094 | 172.2 |
| 4 | 300 | 0.543 | 106.4 | 1.362 | 214.4 |
| 5 | 400 | 0.571 | 111.9 | 1.685 | 265.3 |
| 6 | 500 | 0.572 | 112.2 | 2.00 | 315 |

TABLE 4

Hemoglobin Interference - Decision Level Serum

| Sample | Hb Level | Present Invention mg/dl | % Rec | Wahlefeld method mg/dl | % Rec |
|---|---|---|---|---|---|
| 1 | 0.0 | 1.53 | 100 | 1.56 | 100 |
| 2 | 100 | 1.52 | 99.4 | 1.28 | 82.0 |
| 3 | 200 | 1.53 | 100.1 | 1.38 | 88.8 |
| 4 | 300 | 1.56 | 102.2 | 1.58 | 102.3 |
| 5 | 400 | 1.57 | 102.6 | 1.853 | 119.2 |
| 6 | 500 | 1.57 | 103.1 | 2.22 | 142.9 |

TABLE 5

Hemoglobin Interference - High Abnormal Serum

| Sample | Hb Level | Present Invention mg/dl | % Rec | Wahlefeld method mg/dl | % Rec |
|---|---|---|---|---|---|
| 1 | 0.0 | 6.13 | 100 | 6.13 | 100 |
| 2 | 100 | 6.09 | 99.3 | 5.34 | 87.2 |
| 3 | 200 | 6.05 | 98.6 | 4.89 | 79.8 |
| 4 | 300 | 5.99 | 97.7 | 4.57 | 74.7 |
| 5 | 400 | 5.96 | 97.2 | 4.40 | 71.9 |
| 6 | 500 | 5.92 | 96.5 | 4.32 | 70.6 |

Example VI: Preparation of Direct Bilirubin Reagent

A working color reagent for direct bilirubin analysis was prepared by combining the following ingredients in the following proportions: 0.6 g sulfanilamide, 19.4 g sulfamic acid, 0.5 g sodium nitrite, and sufficient deionized water to bring the total volume to 500 milliters. This reagent remained stable for at least four weeks under refrigeration. To reduce reagent preparation time, or when manufacturing reagents for commercial use, the sodium nitrite and an inert filler such as potassium sulfate, which are dry ingredients, may be added separately to a stock solution containing the sulfanilamide and sulfamic acid. This dry mixture containing the appropriate amount of sodium nitrite is added to the stock sulfanilamide solution, which is in liquid form, to prepare a four-week supply of working color reagent.

Five hundred (500) milliliters of a working acid reagent for direct bilirubin analysis was prepared by combining the following ingredients in the following proportions: 20.0 g betaine monohydrate, 1.0 g TRITON X-100, 1.1 g potassium iodide, 9.7 g sulfamic acid and sufficient deionized water to bring the total volume to 500 milliliters. This reagent also was found to remain stable for at least four-weeks under refrigeration. When manufacturing reagents for commercial use, or to reduce reagent preparation if stability of the reagent for longer than four weeks is required, a stock accelerator reagent containing betaine monohydrate, TRITON X-100, potassium iodide and deionized water can be prepared, to which the appropriate amount of sulfamic acid in dry form is added to prepare a fresh supply of working reagent.

Example VII: Assay for Direct Bilirubin

An assay for direct bilirubin was performed using an Hitachi Model 717 automated blood chemistry analyzer. The reagents were applied and the instrument was configured so that the final reaction mixture contained 12 μl sample, 250 μl working acid reagent and 125 μl working color reagent. The sample and acid reagent were mixed and a blank absorbance reading was made. Color reagent was added and, following a delay time of about 5 minutes, the reaction mixture was measured spectrophotometrically at 546 nm and 660 nm and compared to a the reading obtained from the reaction of a reference material sample containing a known level of conjugated bilirubin.

Example VIII: Linearity of Direct Bilirubin Results

Figure 6:
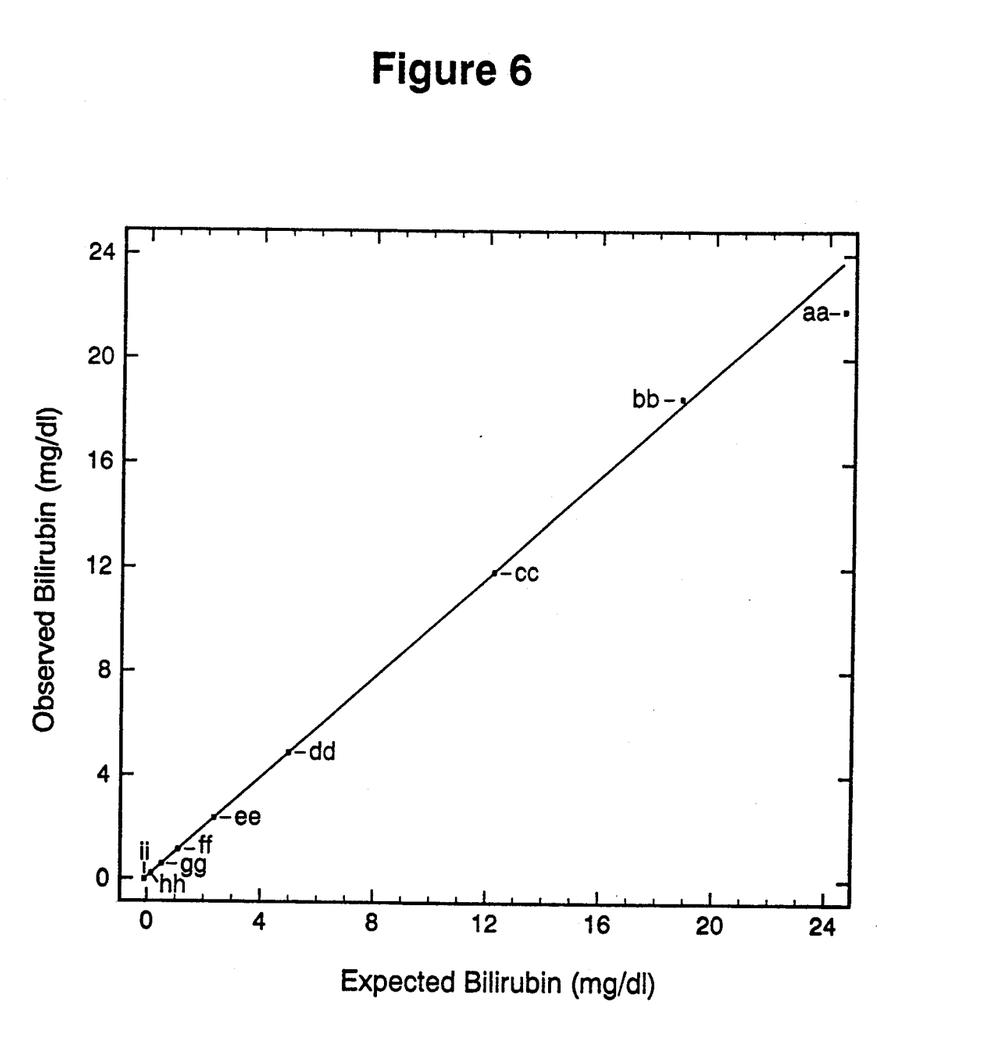
FIG. 6 is a graph illustrating linearity of direct bilirubin results obtained with the method of the present invention up to about 20 mg/dl. Theoretical, or expected results are plotted on the x-axis and the observed results are plotted on the y-axis.

The method described above was used to assay a series of samples prepared from a normal patient serum pool. Aliquots of the pooled serum were spiked with known amounts of conjugated bilirubin. Results obtained are shown in Table 6 below. FIG. 6 is a graph of these results which illustrates linearity of the direct bilirubin results obtained using the method of the present invention to at least about 20 mg/dl. Expected results are plotted along the X-axis and observed results are plotted along the Y-axis and are shown as points aa through ii.

TABLE 6

Linearity - Direct Bilirubin

| Sample | Expected (mg/dl) | Observed (mg/dl) |
|---|---|---|
| aa | 23.4 | 20.88 |
| bb | 18.72 | 17.52 |
| cc | 11.70 | 11.53 |
| dd | 4.68 | 4.84 |
| ee | 2.34 | 2.34 |
| ff | 1.17 | 1.13 |
| gg | 0.59 | 0.57 |
| hh | 0.23 | 0.21 |
| ii | 0.00 | 0.00 |

Example IX: Method Comparison - Direct Bilirubin Assay

Figure 7:
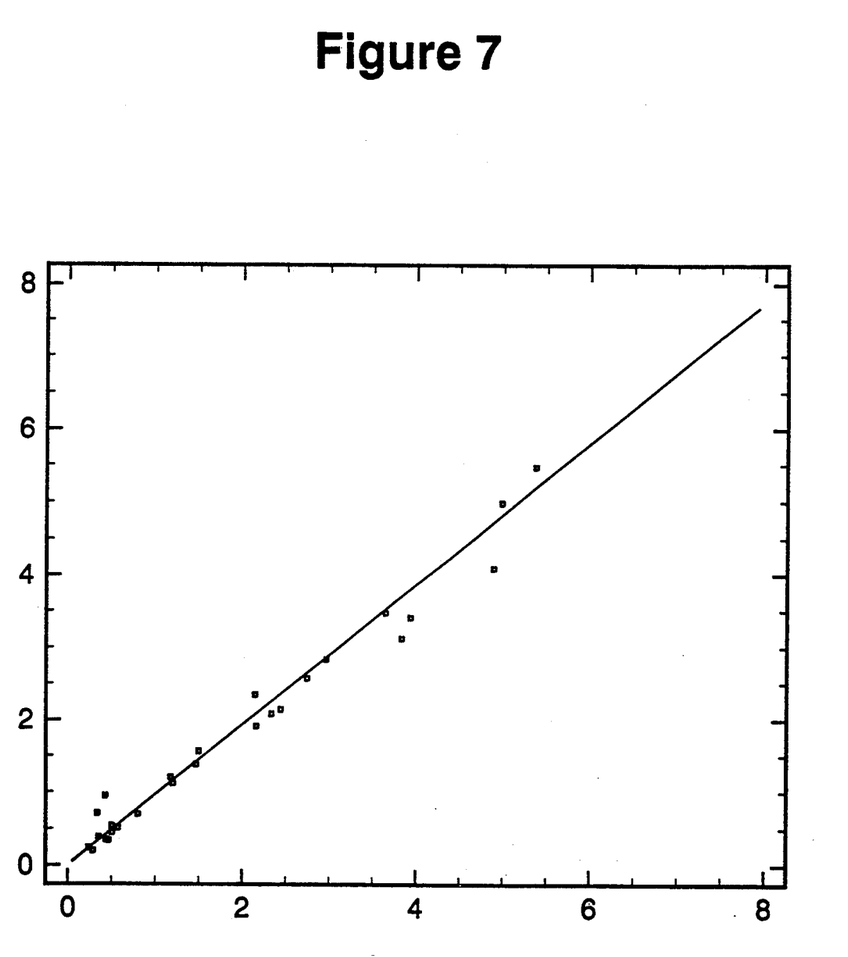
FIG. 7 is a graph showing correlation of direct bilirubin results obtained using the method of the present invention with results obtained using a commercially available method using diazotized sulfanilic acid.

A method correlation study was performed by assaying a group of 30 patient serum samples using the method of the present invention and comparing the results to those obtained on the same samples assayed by a diazo sulfanilic acid method. Actual results obtained are given in Table 7 below. FIG. 7 is a graph of these results. Along the x-axis are plotted the results obtained using the diazo sulfanilic acid method, and the results obtained using the method of the present invention are plotted along the y-axis. Using a least squares linear regression analysis, a correlation coefficient of 0.992 was obtained, with a slope of 0.972 and y-intercept of −0.06.

TABLE 7

Method Comparison - Direct Bilirubin

| Sample | Present Invention (mg/dl) | Diazo Sulfanilic Method (mg/dl) |
|---|---|---|
| 1 | 1.89 | 2.13 |
| 2 | 0.386 | 0.43 |
| 3 | 3.36 | 3.57 |
| 4 | 0.91 | 0.37 |
| 5 | 0.48 | 0.52 |
| 6 | 1.54 | 1.46 |
| 7 | 1.56 | 1.46 |
| 8 | 0.48 | 0.44 |
| 9 | 4.07 | 4.90 |
| 10 | 0.15 | 0.23 |
| 11 | 2.08 | 2.31 |
| 12 | 8.19 | 7.91 |
| 13 | 3.4 | 3.94 |
| 14 | 2.33 | 2.11 |
| 15 | 0.65 | 0.74 |
| 16 | 0.16 | 0.19 |
| 17 | 3.1 | 3.84 |
| 18 | 0.67 | 0.27 |
| 19 | 1.17 | 1.14 |
| 20 | 1.35 | 1.45 |

TABLE 7-continued

Method Comparison - Direct Bilirubin

| Sample | Present Invention (mg/dl) | Diazo Sulfanilic Method (mg/dl) |
|---|---|---|
| 21 | 0.34 | 0.28 |
| 22 | 2.12 | 2.42 |
| 23 | 0.30 | 0.36 |
| 24 | 0.39 | 0.46 |
| 25 | 0.30 | 0.40 |
| 26 | 4.97 | 5.00 |
| 27 | 5.48 | 5.40 |
| 28 | 2.57 | 2.72 |
| 29 | 2.82 | 2.95 |
| 30 | 1.09 | 1.17 |

Example X: Hemoglobin Interference - Direct Bilirubin

Hemoglobin interference studies were conducted using both the method of the present invention and a diazo sulfanilic acid method. Studies were conducted on a serum pool from normal patients, a pool having a total bilirubin value at the medical decision level, and a serum pool with an abnormally high level of bilirubin. Samples from these pools were spiked with varying amounts of hemoglobin up to 500 mg/dl and assayed by both methods. Using the method of the present invention, all levels of conjugated bilirubin showed less than 10% error with the 500 mg/dl hemoglobin spike. The results obtained are listed in Tables 8, 9 and 10 below.

Figure 8:
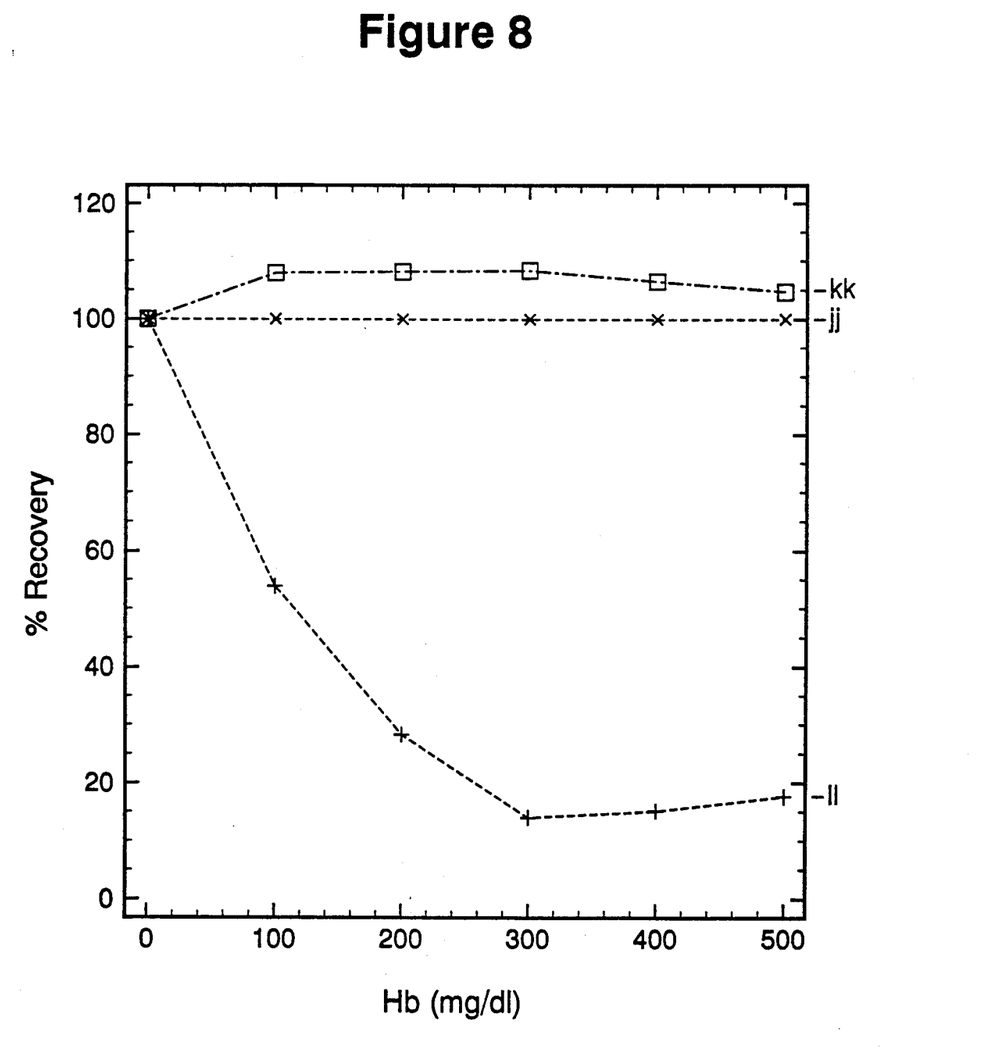
FIG. 8 is a graph showing hemoglobin interference with direct bilirubin results obtained on a normal patient sample using the method of the present invention in comparison with those obtained using the diazo sulfanilic acid method.

FIG. 8 is a graph of the results obtained using the normal serum pool. The percent recovery is plotted on the y-axis and the amount of hemoglobin in mg/dl is plotted on the x-axis. Three curves have been plotted to represent the expected (theoretical) direct bilirubin recovery, shown by line jj; the recovery of total bilirubin obtained using the method of the present invention, shown by line kk; and the recovery of total bilirubin using the diazo sulfanilic acid method, which is shown by line 11.

Figure 9:
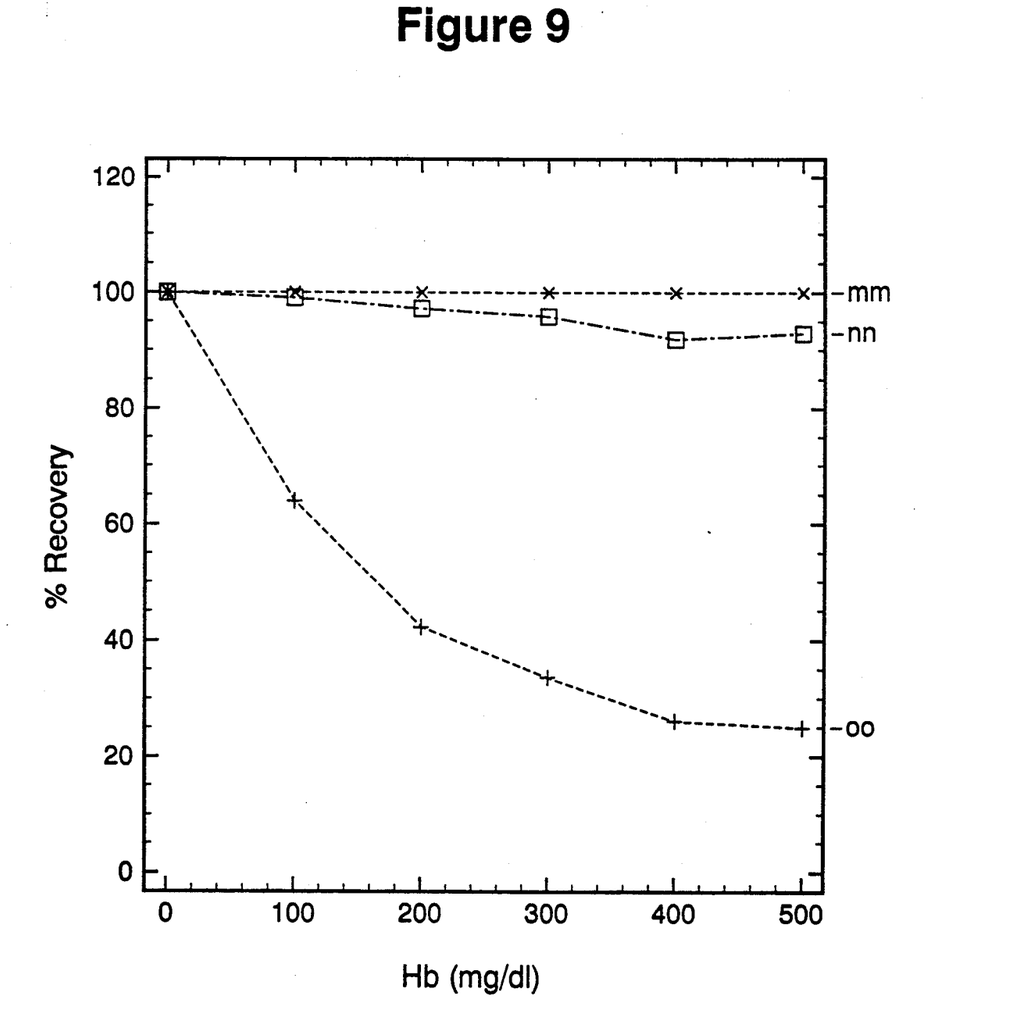
FIG. 9 is a graph showing hemoglobin interference with direct bilirubin results obtained on a medical decision level sample using the method of the present invention in comparison with those obtained using the diazo sulfanilic acid method.

FIG. 9 is a graph of the results obtained using the medical decision level pool. The percent recovery is given on the y-axis and the amount of hemoglobin in mg/dl is given on the x-axis. Three curves have been plotted to represent the expected (theoretical) direct bilirubin recovery, shown by line mm; the recovery of total bilirubin obtained using the method of the present invention, shown by line nn; and the recovery of total bilirubin using the diazo sulfanilic acid method, which is shown by line oo.

Figure 10:
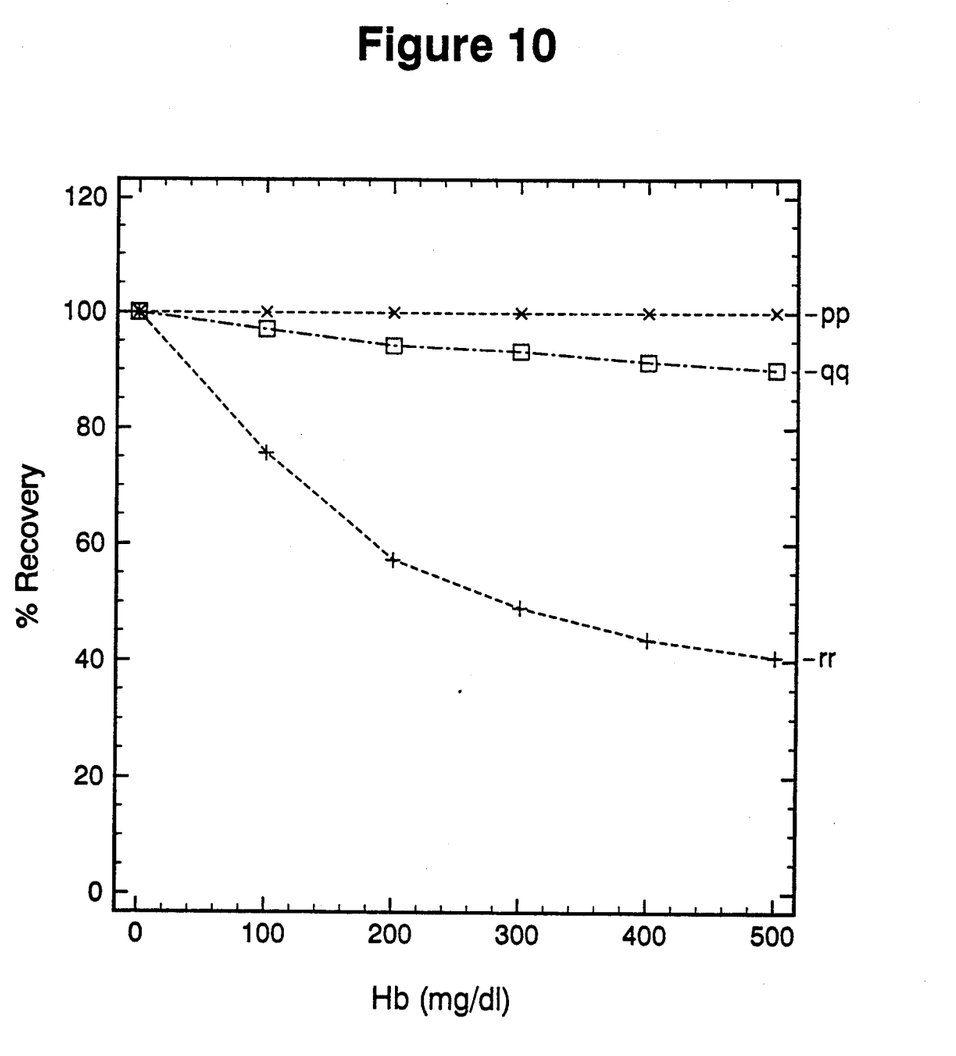
FIG. 10 is a graph showing hemoglobin interference with direct bilirubin results obtained on a high patient sample using the method of the present invention in comparison with those obtained using the diazo sulfanilic acid method.

FIG. 10 is a graph of the results obtained using the high serum pool. The percent recovery is plotted on the y-axis and the amount of hemoglobin in mg/dl is plotted on the x-axis. Three curves have been plotted to represent the expected (theoretical) direct bilirubin recovery, shown by line pp; the recovery of total bilirubin obtained using the method of the present invention, shown by line qq; and the recovery of total bilirubin using the diazo sulfanilic acid method, which is shown by line rr.

TABLE 8

Hemoglobin Interference - Normal Serum

| Sample | Hb Level | Present Invention mg/dl | Present Invention % Rec | Diazo Sulfanilic method mg/dl | Diazo Sulfanilic method % Rec |
|---|---|---|---|---|---|
| 1 | 0.0 | 1.00 | 100 | 0.99 | 100 |
| 2 | 100 | 1.07 | 109.2 | 0.52 | 53.6 |

TABLE 8-continued

Hemoglobin Interference - Normal Serum

| | | Present Invention | | Diazo Sulfanilic method | |
|---|---|---|---|---|---|
| Sample | Hb Level | mg/dl | % Rec | mg/dl | % Rec |
| 3 | 200 | 1.05 | 109.4 | 0.26 | 27.4 |
| 4 | 300 | 1.03 | 109.6 | 0.12 | 12.9 |
| 5 | 400 | 0.99 | 107.8 | 0.13 | 14.3 |
| 6 | 500 | 0.95 | 106 | 0.15 | 16.8 |

TABLE 9

Hemoglobin Interference - Decision Level Serum

| | | Present Invention | | Diazo Sulfanilic method | |
|---|---|---|---|---|---|
| Sample | Hb Level | mg/dl | % Rec | mg/dl | % Rec |
| 1 | 0.0 | 2.66 | 100 | 2.67 | 100 |
| 2 | 100 | 2.60 | 99.7 | 1.67 | 63.8 |
| 3 | 200 | 2.50 | 97.9 | 1.07 | 41.7 |
| 4 | 300 | 2.42 | 96.8 | 0.83 | 33.1 |
| 5 | 400 | 2.31 | 92.4 | 0.64 | 25.5 |
| 6 | 500 | 2.24 | 93.6 | 0.58 | 24.2 |

TABLE 10

Hemoglobin Interference - High Abnormal Serum

| | | Present Invention | | Diazo Sulfanilic method | |
|---|---|---|---|---|---|
| Sample | Hb Level | mg/dl | % Rec | mg/dl | % Rec |
| 1 | 0.0 | 6.30 | 100 | 6.25 | 100 |
| 2 | 100 | 6.04 | 97.8 | 4.65 | 75.9 |
| 3 | 200 | 5.74 | 94.9 | 3.42 | 57 |
| 4 | 300 | 5.58 | 94.2 | 2.86 | 48.7 |
| 5 | 400 | 5.33 | 92.0 | 2.48 | 43.1 |
| 6 | 500 | 5.14 | 90.6 | 2.25 | 40.0 |

Example XI: Indican Interference

To study the effect of indican on recovery of total bilirubin using the method of the present invention, each of eight samples in a commercially available linearity set was spiked with a fresh indican stock solution resulting in a 1 millimole/liter final concentration of indican in each sample. Total bilirubin results obtained are given in Table 11 and show no indican interference using the method of the present invention in contrast to extremely marked interference seen when using the method of Wahlefeld.

TABLE 11

Indican Interference - Total Bilirubin

| | Present Invention Method | | | Wahlefeld method | | |
|---|---|---|---|---|---|---|
| | Without Indican | With Indican | | Without Indican | With Indican | |
| Sample | mg/dl | mg/dl | % Rec | mg/dl | mg/dl | % Rec |
| L-0 | 0.29 | 0.31 | 106.9 | 0.44 | 2.38 | 540.9 |
| L-0.5 | 1.41 | 1.41 | 100 | 1.50 | 3.48 | 232 |
| L-1 | 2.55 | 2.56 | 100.4 | 2.65 | 4.59 | 173.2 |
| L-2 | 4.70 | 4.77 | 101.5 | 4.77 | 6.79 | 142.3 |
| L-4 | 8.87 | 8.96 | 101.0 | 9.02 | 10.86 | 120.4 |
| L-6 | 13.28 | 13.27 | 99.9 | 13.47 | 15.14 | 112.4 |
| L-8 | 17.60 | 17.58 | 99.9 | 17.89 | 19.66 | 109.9 |
| L-10 | 22.07 | 21.98 | 99.6 | 22.35 | 23.73 | 106.2 |

Example XII: Lipemia Interference

To study the effect of lipemia on recovery of total bilirubin using the method of the present invention, aliquots from a lipemic plasma sample with a lipemic index of 313 and from a normal serum sample were spiked with varying levels of bilirubin and assayed by both the method of the present invention and the Wahlefeld method. Total bilirubin results obtained are given in Table 12 and show no lipemia interference using the method of the present invention in contrast to marked interference seen when using the method of Wahlefeld.

TABLE 12

Lipemia Interference

| | | Present Invention | | Wahlefeld method | |
|---|---|---|---|---|---|
| Sample | Theoretical (mg/dl) | normal serum (mg/dl) | lipemic plasma (mg/dl) | normal serum (mg/dl) | lipemic plasma (mg/dl) |
| 1 | 0.0 | 0.71 | 0.04 | 0.23 | 2.04 |
| 2 | 1.5 | 1.58 | 1.59 | 1.67 | 3.28 |
| 3 | 2.5 | 2.96 | 2.85 | 2.96 | 4.77 |
| 4 | 5.0 | 5.63 | 5.59 | 5.67 | 7.45 |
| 5 | 10.0 | 10.47 | 10.3 | 10.51 | 12.2 |

What is claimed is:

1. A reagent composition for the measurement of bilirubin in a sample comprising a diazonium salt, iodide ions, an acid and at least one betaine selected from the group consisting of alkyl betaine, betaine and betaine hydrate.

2. The composition of claim 1 in which the diazonium salt is sulfanilamide diazonium salt.

3. The composition of claim 1 in which the acid is sulfamic acid.

4. The composition of claim 1 in which the betaine is present in an amount between 1 and 20 percent by weight.

5. The composition of claim 1 further comprising a nonionic surfactant.

6. The composition of claim 2 in which the sulfanilamide diazonium salt is present in an amount less than 20 millimolar.

7. A reagent composition for the measurement of total bilirubin in a sample comprising alkyl betaine derived from a C12-C14 alcohol, a diazonium salt, iodide ions and an acid.

8. The composition of claim 7 in which the diazonium salt is sulfanilamide diazonium salt.

9. The composition of claim 7 in which the acid is sulfamic acid.

10. The composition of claim 7 in which the alkyl betaine is present in an amount between 1 and 20 percent by weight.

11. The composition of claim 7 further comprising a nonionic surfactant.

12. The composition of claim 8 in which the sulfanilamide diazonium salt is present in an amount less than 20 millimolar.

13. A reagent composition for the measurement of conjugated bilirubin in a sample comprising a diazonium salt, iodide ions, an acid and at least one betaine selected from the group consisting of alkyl betaine, betaine and betaine hydrate.

14. The composition of claim 13 in which the diazonium salt is sulfanilamaide diazonium salt.

15. The composition of claim 13 in which the acid is sulfamic acid.

16. The composition of claim 13 in which the betaine is present in an amount between 1 and 20 percent by weight.

17. The composition of claim 13 further comprising a nonionic surfactant.

18. The composition of claim 14 in which the sulfanilamide diazonium salt is present in an amount less than 20 millimolar.

19. A method for the determination of bilirubin in a sample suspected of containing bilirubin comprising contacting said sample with a reagent composition comprising a diazonium salt, iodide ions, an acid and at least one betaine selected from the group consisting of alkyl betaine, betaine and betaine hydrate, and measuring the color produced as a measure of the bilirubin in the sample.

20. A test kit for the determination of bilirubin comprising components which can be combined to form a reagent composition comprising a diazonium salt, iodide ions, an acid and at least one betaine selected from the group consisting of alkyl betaine, betaine and betaine hydrate.

21. In a reagent composition for the measurement of total bilirubin in a sample, said reagent composition comprising a diazonium salt, the improvement wherein the reagent composition also comprises between 1 and 20 percent by weight of an alkyl betaine derived from a C12–C14 alcohol.

* * * * *